United States Patent
Haras

(10) Patent No.: US 9,192,349 B2
(45) Date of Patent: Nov. 24, 2015

(54) COMPUTED TOMOGRAPHY DEVICE AND METHOD AND DATA STORAGE MEDIUM FOR OPERATION THEREOF

(75) Inventor: Gabriel Haras, Muecke (DE)

(73) Assignee: Siemens Aktiengesellschaft, Munich (DE)

(*) Notice: Subject to any disclaimer, the term of this patent is extended or adjusted under 35 U.S.C. 154(b) by 1000 days.

(21) Appl. No.: 13/311,890

(22) Filed: Dec. 6, 2011

(65) Prior Publication Data

US 2012/0143659 A1  Jun. 7, 2012

(30) Foreign Application Priority Data

Dec. 6, 2010 (DE) .......................... 10 2010 062 459

(51) Int. Cl.
*A61B 6/00* (2006.01)
*G06Q 30/00* (2012.01)
*G06Q 30/02* (2012.01)

(52) U.S. Cl.
CPC ............ *A61B 6/545* (2013.01); *G06Q 30/0207* (2013.01); *H01J 2235/00* (2013.01)

(58) Field of Classification Search
CPC .. A61B 6/0306; A61B 6/4085; A61B 6/0312; A61B 6/545; A61B 6/56; A61B 6/032; A61B 6/4014; A61B 6/4266; A61B 6/027; A61B 6/488; A61B 6/542; A61B 6/06; A61B 6/405; A61B 6/4488; A61B 6/482; A61B 6/5258; A61B 6/544; A61B 6/583; A61B 5/055; A61B 6/037; A61B 6/08; A61B 6/4007; A61B 6/4021; A61B 6/4028; A61B 6/4035; G06Q 30/0207; H01J 2235/00; H01R 39/56

USPC ............................................. 378/4, 15, 9, 62
See application file for complete search history.

(56) References Cited

U.S. PATENT DOCUMENTS

| | | |
|---|---|---|
| 5,696,807 A | 12/1997 | Hsieh |
| 2004/0125624 A1 | 7/2004 | Scheel et al. |
| 2005/0078795 A1 | 4/2005 | Kawabuchi |
| 2006/0153335 A1 | 7/2006 | Ishikawa et al. |
| 2009/0238329 A1 | 9/2009 | Haras |
| 2009/0252286 A1 | 10/2009 | Mukumoto et al. |
| 2009/0262892 A1 | 10/2009 | Haras |

FOREIGN PATENT DOCUMENTS

| | | |
|---|---|---|
| DE | 203 21 723 U1 | 4/2009 |
| JP | 04-049613 | 2/1992 |
| JP | H06292361 A | 10/1994 |
| WO | WO-2010/128416 A2 | 11/2010 |

*Primary Examiner* — Irakli Kiknadze
(74) *Attorney, Agent, or Firm* — Schiff Hardin LLP

(57) ABSTRACT

In a method for operating a computed tomography device for reducing the load on at least one technical component of the computed tomography device during operation of the at least one technical component, as well as a computed tomography device and a data storage medium that implement such a method, for at least one scan parameter of the computed tomography device affecting the at least one technical component an extreme value is defined, the method being an operating mode for the computed tomography device is selected in which the settable value for the at least one scan parameter affecting the at least one technical component is limited to a certain percentage below or above the extreme value for the operation of the at least one technical component.

18 Claims, 2 Drawing Sheets

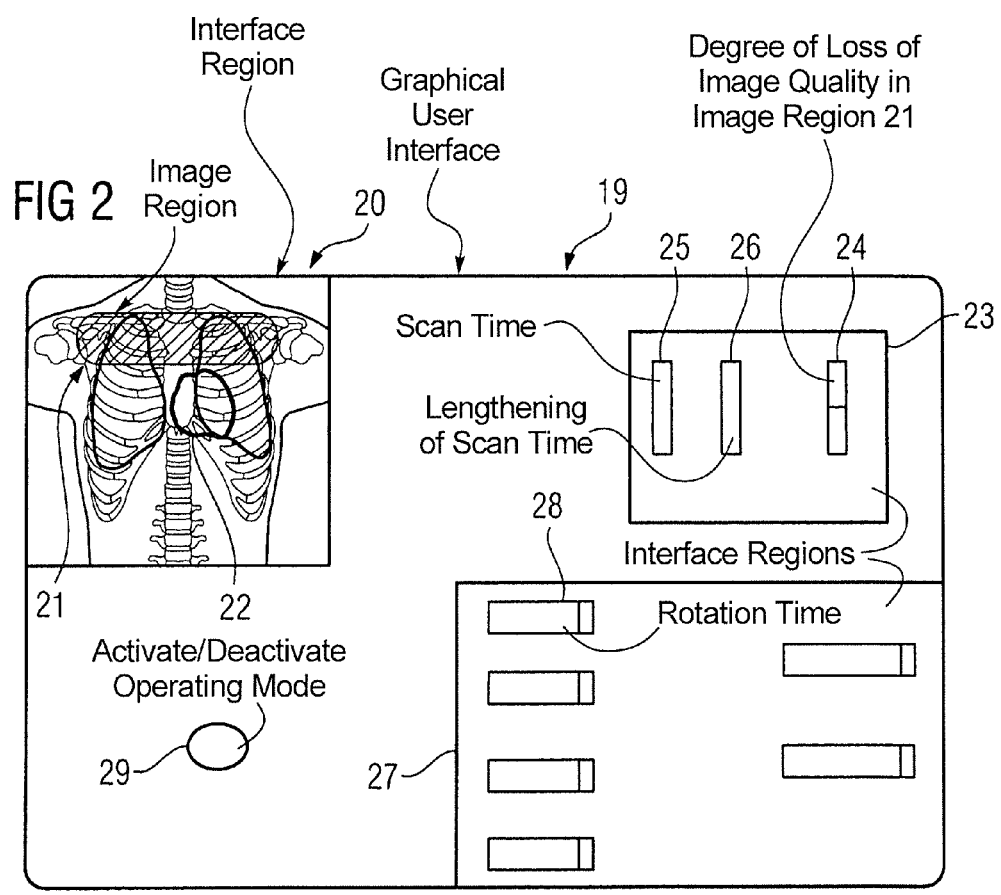

COMPUTED TOMOGRAPHY DEVICE AND METHOD AND DATA STORAGE MEDIUM FOR OPERATION THEREOF

BACKGROUND OF THE INVENTION

1. Field of the Invention

The present invention relates to a method for operating a computed tomography device for reducing the load on at least one technical component of the computed tomography device during operation of the at least one technical component. The invention also relates to a non-transitory computer-readable data storage medium encoded with programming instructions for implementing such a method, and a computed tomography device operable according to the method.

2. Description of the Prior Art

A computed tomography device, in particular a third generation computed tomography device, embodies a number of technical components, which during operation of the computed tomography device are subject to a significant load and are therefore subject to age or wear. The ageing and wear are generally greater or more marked, the closer the respective technical component is operated to its load limit.

Such a technical component is, for example, an x-ray tube of a computed tomography device. The service life of an x-ray tube is influenced significantly by the strength of the tube currents used during operation of the x-ray tube. Major temperature fluctuations are a particular problem, resulting in particular from secondary electrons striking the beam outlet window of the x-ray tube. The temperature here rises in a linear manner with the tube current used. In particular x-ray tubes frequently operated close to or at their maximum permissible tube current therefore age more quickly and often have to be replaced prematurely, thereby incurring not insignificant costs.

Further technical components of the computed tomography device, which during operation at or close to their load limit are subject to increased wear, are bearings for the rotating support of the rotatable part relative to the stationary part of the gantry and slip rings for the transmission of data and/or energy between the rotatable and stationary parts of the gantry of the computed tomography device.

The reason why technical components are operated at their load or performance limit is frequently due to the operation of a computed tomography device that has technical components for cost reasons have a low reserve capacity, with automatic program systems, e.g. automatic dose systems, with which the tube current of the x-ray tube of the computed tomography device is modulated as a function of the rotation angle and therefore of the body cross section of a patient to be irradiated, in order to reduce the dose of x-ray radiation to be applied to a patient whilst still ensuring the best possible image quality. The tube current is reduced, for example for x-ray projections in an anterior-posterior direction, and is increased for x-ray projections in a lateral direction, where beam attenuation is greater. The automatic dose system therefore ensures that the patient is scanned with minimal exposure. In order also to be able to obtain high quality image information from an adipose patient, who generally demonstrates greater beam attenuation than a patient of normal weight, the automatic dose system must frequently increase the tube current so that the x-ray tube with low reserve capacity is operated close to or at its maximum permissible tube current, with the result that it is subject to a significant load and therefore premature ageing.

SUMMARY OF THE INVENTION

An object of the invention is to specify a method, a data medium and a computed tomography device of the type described above with which the load on at least one technical component of the computed tomography device is reduced during operation of the computed tomography device.

According to the invention this object is achieved by a method for operating a computed tomography device for reducing the load on at least one technical component of the computed tomography device during operation of the at least one technical component, wherein an extreme value is defined for at least one scan or operating parameter of the computed tomography device affecting the technical component, the method being an operating mode for the computed tomography device, in which operating mode the settable value for the at least one scan or operating parameter affecting the technical component is limited to a certain percentage below or above the extreme value for operation of the technical component.

The invention is based on the consideration of providing an operating mode, specifically a type of "economy mode" for a computed tomography device, in which for at least one, preferably more than one, technical component of the computed tomography device, based on maximum or minimum permissible scan or operating parameters defined for the technical components, it is only permitted to set values for the scan or operating parameters that are below the defined maximum permissible values or above the defined minimum permissible values. For example only values that are 10% or more below the maximum permissible values or above the minimum permissible values are permitted. While other operating modes are intended to optimize image quality for example, the object of the inventive operating mode is to reduce the load on technical components of the computed tomography device, in order to delay the ageing or wear of the technical components and therefore their replacement.

The operating mode can involve, for example, a modified automatic dose system, which is designed not only to reduce the dose of x-ray radiation to be applied to a patient but also to subject technical components of the computed tomography device to the smallest possible load. In this process losses of image quality can knowingly be accepted, as long as they are still acceptable for imaging purposes or occur in image regions that are not relevant for the intended diagnosis for example.

According to one embodiment of the invention the at least one technical component is at least one x-ray tube, at least one slip ring for the transmission of data and/or energy between a rotatable and stationary part of a gantry and/or at least one bearing for the rotating support of the rotatable part relative to the stationary part of the gantry of the computed tomography device.

According to a further embodiment of the invention the settable value for the tube current and/or the mean power consumption of the at least one x-ray tube per circuit of the rotatable part of the gantry and/or the tube voltage and/or the size of the focus on the anode of the x-ray tube is limited as the scan or operating parameter for the at least one x-ray tube. This prevents the x-ray tube being operated close to or at its load limit, thereby avoiding premature ageing due to high operating temperatures and therefore premature replacement of the x-ray tube. For example, the tube current is limited to 90% of its maximum permissible value as set by the manufacturer. The size of the focus, i.e. its flat extension on the surface of the anode, can also be limited so that it is 10% above its minimum permissible value, in order to reduce the thermal load on the anode of the x-ray tube, in particular the focal path on the anode and therefore its abrasion during operation.

In one variant of the invention the size of the focus on the anode of the x-ray tube is set as a function of a scan or recording protocol of the computed tomography device and/or of a certain examination of a patient. For clinical problems where the image definition is less relevant, for example for examinations or scans of soft parts such as the brain or liver, it can be specified in a corresponding scan or recording protocol that a relatively large focus is used, to reduce the thermal load on the anode of the x-ray tube. For problems where image definition is a priority, for example examinations or scans of bones, comparatively small focus sizes are set. As mentioned above, focus size is preferably set in a protocol-specific manner and above the defined minimum value for focus size.

According to another embodiment of the invention the settable value for the rotation speed or rotation time and/or pitch is limited as the scan or operating parameter for the at least one slip ring or the at least one bearing. A short rotation time and a high rotation speed or circuit speed or high pitch, which refers to the relationship of table advance per rotation to slice collimation, increase the load on the bearing and the wear at slip rings. Therefore if there is an upward limit for the rotation speed and a downward limit for the rotation time and/or an upward limit for the pitch, the load on the bearing(s) and slip ring(s) of the computed tomography device is reduced.

According to a further variant of the invention in the operating mode at least one operating function or at least one type of operation of the computed tomography device is deactivated, in particular if this subjects the technical components of the computed tomography device to a greater load than an alternatively available operating function or type of operation.

In this context according to one embodiment of the invention the "sequence scan" operating function or type of operation is deactivated, as a sequence scan subjects the technical components of the computed tomography device to a greater load than for example the alternatively available spiral scan operating function or type of operation.

In one embodiment of the invention the operating mode can be activated and deactivated as desired by a user. This means that the operating mode or "economy mode" can be deactivated in particular when the entire capacity of the computed tomography device is required. To this end for example a graphical user interface having a button for activation and deactivation purposes can be provided.

However "economy mode" can also be deactivated if the user changes the settable value of a scan or operating parameter affecting at least one technical component beyond its predefined limit or extreme value, so that it is outside the range defined for "economy mode". The user is preferably informed of deactivation and the reason for deactivation of "economy mode" in an information window of the graphical user interface. In such an instance it is no longer possible to actuate the activation button. Activation of "economy mode" is only possible again when the conditions for it are satisfied again, i.e. when the values of the relevant scan or operating parameters are back within the predefined limits.

According to one variant of the invention, if the value provided in a certain recording or scan protocol for a certain examination of a patient for the scan or operating parameter affecting the at least one technical component cannot be set as a consequence of the limiting of the settable value for the at least one scan or operating parameter, the value for the scan or operating parameter affecting the at least one technical component is set to the certain percentage below or above the extreme value and the value of another scan or operating parameter is preferably adjusted automatically so that the examination of the patient can still preferably take place with the desired image quality. According to a further variant of the invention the other scan or operating parameter is the scan time.

If, for example as a consequence of the limiting of the value of the tube current in "economy mode", the level of the tube current provided for the patient examination cannot be set at all or even just temporally, the scan time is lengthened automatically in a corresponding manner, so that the scan or examination of the patient can still be performed. In instances where the conflict cannot be resolved by lengthening the scan time, for example because there is a concern about motion artifacts, the scan must be performed outside "economy mode".

According to another variant of the invention a tube load computer checks the feasibility of an intended scan or examination of a patient for the at least one x-ray tube for the scan or operating parameters affecting the at least one x-ray tube. If necessary the tube load computer prompts the adjustment of a scan or operating parameter, such as scan time, so that the examination of the patient can take place. Therefore the tube load computer checks before the examination or scan for example based on the attenuation values of a topogram recorded for the patient, the current temperature of the x-ray tube, etc., whether the intended examination or scan of the patient can be performed with the desired scan or operating parameters.

According to a further embodiment of the invention consequences associated with the operating mode or "economy mode" for a scan of a patient and/or for image information relating to the patient that can be obtained further to a scan of the patient are visualized. A lengthening of the scan time associated with the limiting of the rotation time or the tube current and/or a loss of achievable image quality associated with the limiting of the tube current are preferably visualized.

According to one variant of the invention the body region of the patient where and/or the degree to which a loss of image quality takes place is visualized. Reference can be made inter alia here to the method described in DE 10 2008 014 737 A1. The graphical user interface already mentioned above is preferably used for this.

According to one embodiment of the invention the use of the operating mode is logged and/or visualized all the time during operation of the computed tomography device. Logging takes place as it were in the background from first commissioning to the final stoppage of the computed tomography device. Visualization can again take place based on the graphical user interface.

According to a further embodiment of the invention logging of the use of the operating mode by a customer and user of the computed tomography device is used as the basis for calculating discounts granted to the customer of the computed tomography device in the context of a service agreement relating to the computed tomography device or to incentivize the customer of the computed tomography device. Incentivization can involve for example an extension of the manufacturer's warranty, etc. In this way the customer of the computed tomography device is motivated to use the operating mode or "economy mode" as frequently as possible.

The object underlying the present invention is also achieved by a data storage medium encoded with programming instructions that implement any or all embodiments of the method described above. The object is also achieved by a computed tomography device with a control unit configured to implement any or all embodiments of the method described above.

BRIEF DESCRIPTION OF THE DRAWINGS

FIG. 2 shows a graphical user interface of the x-ray computed tomography device of FIG. 1.

DESCRIPTION OF THE PREFERRED EMBODIMENTS

Figure 1:
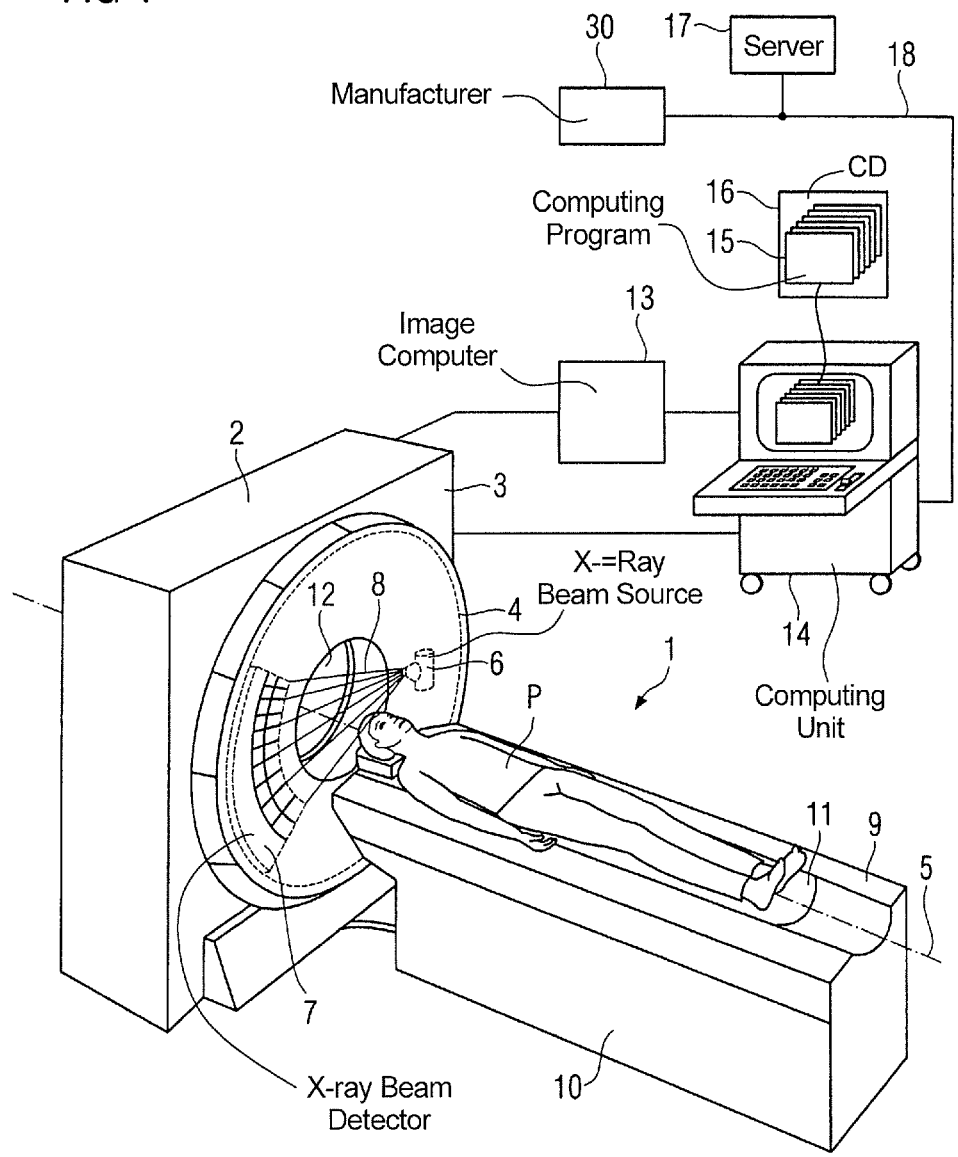
FIG. 1 shows an x-ray computed tomography device operable in accordance with the invention.

Elements that are identical or have an identical function are shown with the same reference characters in all the figures. The diagrams in the figures are schematic and not necessarily to scale. The x-ray computed tomography device 1 illustrated in FIG. 1 is only explained as far as is necessary for an understanding of the invention in the following and without restriction of generality.

The computed tomography device 1 shown in FIG. 1 has a gantry 2 with a stationary part 3 and with a schematically outlined part 4 that can be rotated about a system axis 5 and is supported by means of a bearing (not shown in FIG. 1) in a rotatable manner in relation to the stationary part 3. In the present exemplary embodiment of the invention the rotatable part 4 features an x-ray system, which comprises an x-ray beam source 6 and an x-ray beam detector 7, which are disposed facing one another on the rotatable part 4. During operation of the computed tomography device 1 x-ray radiation 8 is emitted from the x-ray beam source 6 in the direction of the x-ray beam detector 7, penetrates a measurement object and is detected by the x-ray beam detector 7 in the form of measurement data or measurement signals.

The computed tomography device 1 also features a patient couch 9 to support a patient P to be examined. The patient couch 9 comprises a couch base 10, on which a patient support plate 11 actually provided to support the patient P is disposed. The patient support plate 11 can be moved by motor relative to the couch base 10 in the direction of the system axis 5 in such a manner that it can be introduced, together with the patient P, into the opening 12 in the gantry 2 for the recording of 2D x-ray projections of the patient P, e.g. in a spiral scan.

The computational processing of the 2D x-ray projections recorded using the x-ray system and the reconstruction of slice images, 3D images or a 3D data record based on the measurement data or measurement signals of the 2D x-ray projections take place using a schematically illustrated image computer 13 of the computed tomography device 1.

The computed tomography device 1 also features a computing unit 14, which can be and is used to execute computing programs to operate and control the computed tomography device 1. The computing unit 14 here does not have to be configured as a separate computing unit 14 but can also be integrated in the computed tomography device 1.

In the present exemplary embodiment of the invention a computing program 15 is loaded into the computing unit 14 to implement a method for reducing the load on at least one technical component of the computed tomography device 1 during operation of the technical component or the computed tomography device 1. The computing program 15 here is a specific operating mode for the computed tomography device 1 and can be loaded into the computing unit 14 from a portable data medium, e.g. from a CD 16 or a memory stick, or even from a server 17 by way of a network 18, which can be a public network or an internal clinic or hospital network.

In the present exemplary embodiment of the invention the operating mode is a modified automatic dose system, which in the present exemplary embodiment can also be referred to as "economy mode", which besides the dose modulation to scan the patient P with a low level of exposure is designed to subject the technical components of the computed tomography device 1 to the smallest possible load, in that at least one threshold value is set for at least one settable scan parameter for at least one or more technical components so that the respective technical component is not operated at its load limit, instead being operated below this.

In the present exemplary embodiment of the invention the technical components to be preserved are the x-ray beam source 6 or x-ray tube 6, the bearing for the rotating support of the rotatable part 4 relative to the stationary part 3 of the gantry 2 and slip rings (not shown but known per se) for the transmission of data and/or energy between the rotatable part 4 and stationary part 3 of the gantry 2.

In the case of the x-ray tube 6, the manufacturer of the x-ray tube 6, for example, predefines or defines an extreme value or a value for the maximum permissible tube current. In the present operating mode, to preserve the x-ray tube 6, in addition to the maximum permissible tube current set by the manufacturer a threshold value is also predefined or set for the tube current, which in the present exemplary embodiment of the invention is 10% below the maximum permissible tube current. For the "tube current" scan parameter it is therefore only possible to set a value that is 10% or more below the maximum permissible tube current in the operating mode. Similarly for the scan parameter of the mean power consumption of the x-ray tube 6 per circuit of the rotatable part 4 around the stationary part 3 of the gantry 2 a threshold value is set so that mean power consumption is a certain percentage below the maximum permissible power consumption per se of the x-ray tube 6 per circuit of the rotatable part 4 around the stationary part 3 of the gantry 2. This prevents the x-ray tube 6 being operated at its power limit or ensures that the x-ray tube 6 is operated within a range which does not subject the x-ray tube 6 to an undue load and does not result in premature ageing requiring premature replacement of the x-ray tube 6.

A threshold value is also set for the size of the focus on the anode (not specifically illustrated) of the x-ray tube 6. Since the load on the x-ray tube 6, in particular the anode of the x-ray tube 6, increases as the size of the focus decreases, the threshold value is set so that the size of the focus in the present exemplary embodiment of the invention must be at least 10% larger than the minimum permissible size of the focus.

In the exemplary embodiment of the invention the size of the focus on the anode of the x-ray tube 6 is preferably also set as a function of a scan protocol or the intended examination of a patient P. While for example during soft part examinations, in which image definition is of minor relevance, the focus is comparatively large, the focus for bone examinations for example, in which image definition is a priority, is by comparison reduced. In "economy mode" it does not however drop below the defined threshold value based on the extreme value.

To preserve the bearing for the rotating support of the rotatable part 4 relative to the stationary part 3 and the slip rings from excessive loading and abrasion, which occur primarily at high rotation speeds or with short rotation times of the rotatable part 4 relative to the stationary part 3 of the gantry 2, in the exemplary embodiment of the invention the settable values for rotation speed and pitch are limited as scan parameters in the operating mode, to which end a threshold value is again predefined in each instance, which is a certain percentage below the maximum value per se. This ensures that the bearing and slip rings, the replacement, in particular premature replacement, of which would be associated with high costs for an operator or user of the computed tomography device 1, are operated in a preserving fashion and with a smaller load.

In the exemplary embodiment of the invention in the operating mode the "sequence scan" operating function or type of operation is also deactivated, so that sequence scans are not possible, in which 2D x-ray projections of the patient are recorded from different directions in different successive table positions by rotating the x-ray system around the patient P. As the 2D x-ray projections are being recorded, the patient support plate 10 holding the patient is not moved. It is only moved between recordings to dispose the x-ray system relative to a different body segment of the patient. Such a sequence scan subjects the x-ray tube 6 to a significant load due to the repeated activation of the x-ray tube 6 and the resulting fast temperature changes. In the operating mode therefore only spiral scans are possible, in which the x-ray tube 6 is operated continuously. Also the maximum rotation speed is limited, to reduce the load on the bearing and the slip rings.

If the "economy mode" operating mode is selected and the scan parameters of a similarly selected recording and scan protocol for the examination of a patient satisfy the limit and threshold values of "economy mode", the scan or examination of the patient can be performed directly.

Generally a tube load computer (not shown) for the x-ray tube 6 checks the feasibility of the scan or examination of the patient P for the scan parameters affecting the x-ray tube 6. Based on the attenuation values of a topogram of the patient P recorded before the examination or scan, it is checked taking into account the current temperature of the x-ray tube 6, the scan time, the millisecond-ampere product, the tube voltage, the length of the body region to be scanned, the table advance, etc., whether the scan can be performed with the desired scan parameters.

As a result of the operating mode it can occur that, for example, the value of the tube current to be set according to a scan protocol cannot be set, as it is above the limit or threshold value of "economy mode". In such an instance the user can deactivate "economy mode" or adjust one or more other scan parameters of the scan protocol in order to be able to perform the scan even with limited tube current. The adjustment of the one or more scan parameters preferably takes place automatically, for example by means of the tube load computer. In the case of a tube current reduced by the "economy mode", the scan time for example, in other words the time required for the scan, is automatically lengthened, in order to be able to perform the scan with the desired image quality. As a consequence of the limiting of the rotation speed and pitch, there can also be an automatic or even manually performed increase of the scan time, in order to be able to perform the examination of the patient at all.

As a consequence of the "economy mode", in particular due to the limiting of the tube current, instances can also occur in which, despite a lengthening of the scan time, when certain body regions of a patient are being scanned, such as the shoulder region, or when adipose patients are being scanned, the image quality may not be ideal due to the significant attenuation of the x-ray beams by the body tissue.

In all these instances the consequences associated with the operating mode are visualized for a user of the computed tomography device 1, preferably in a graphical user interface. FIG. 2 shows such a graphical user interface 19 schematically.

In the present exemplary embodiment of the invention the graphical user interface 19 features a region 20, in which a topogram of the patient P, generally recorded before a scan of the patient P, is displayed. In the present exemplary embodiment of the invention the topogram visualizes the region 21, in which a loss of achievable image quality has to be accepted due to the operating mode. This allows a user to identify immediately whether or not the loss is acceptable. If the heart 22 of the patient is to be scanned primarily, the loss of image quality in the shoulder region of the patient P is of minor importance, so the scan can be performed as planned.

In one region 23 of the graphical user interface 19 the bar 24 is also used to visualize the degree of loss of image quality in the region 21 in the form of a percentage indication. The scan time 25 and a lengthening 26 of the scan time due to the operating mode are also visualized in the region 23.

In the region 27 further scan parameters, such as for example the rotation time 28, etc., are visualized. The graphical user interface 19 also has a button 29, which is used to activate and deactivate the operating mode. If the loss of image quality is not acceptable to a user for example, said user can deactivate the operating mode or "economy mode" and scan the patient using an alternative operating mode.

In the present exemplary embodiment of the invention the use of the operating mode is logged by the operator of the computed tomography device 1 all the time during operation of the computed tomography device 1, i.e. from its first commissioning to final stoppage, for example in an event log file of the computing unit 14. The rate of use of the operating mode can be visualized for the operator of the computed tomography device 1 based on the log using the graphical user interface 19.

It is also possible for the manufacturer 30 of the computed tomography device 1 or a service company carrying out maintenance work on the computed tomography device 1 to request the event log file for example by way of the network 18. It is also possible to send the event log file preferably regularly via email to the service company or manufacturer 30 of the computed tomography device 1. The log of the use of the operating mode can then be used as a basis for calculating discounts to be granted to the user of the computed tomography device 1 in the context of a service agreement relating to the computed tomography device or to incentivize the user of the computed tomography device. By using the operating mode the customer can thus reduce costs incurred in the context of a service agreement, if it is stated in the agreement with the service company, which may also be the manufacturer of the computed tomography device, which discounts are granted to the customer as a function of the use of the operating mode. Similarly it can be agreed with the manufacturer of the computed tomography device 1, to extend the manufacturer's warranty for the computed tomography device 1 as a function of the use of the operating mode as an inventive, the customer being able to gain financial benefit from this in a similar manner.

In contrast to the described exemplary embodiment of the invention values to be set for scan or operating parameters for further technical components of the computed tomography device can also be limited so that the respective value is a certain percentage below or above a defined extreme value for the respective technical component, in order to reduce the load on the respective technical component during operation of the technical component. The setting of a threshold or limit value is based here on the capacity of the respective technical component in each instance. The setting of a threshold or limit value does not necessarily have to take place as described above by way of example such that the threshold or limit value is 10% below or above the extreme value. Instead other percentages or steps are also possible.

As a result of the invention therefore the technical components of a computed tomography device are subject to less stress, thereby allowing their service lives to be lengthened in an advantageous manner. In some instances the user of the computed tomography device must accept a slightly poorer image quality. In most instances the deterioration in image quality is so small however that the user will not automatically notice it. In the case of scans performed with a low dose anyway, for example scans of children or organs such as the lung, the usual image quality is maintained. Even with adipose patients a slightly poorer image quality is generally only to be expected in certain body regions, such as the shoulder region or the pelvic region.

In contrast to the described exemplary embodiment of the invention the automatic dose system and "economy mode" operating modes do not have to be combined. Instead both modes can exist and be activated and deactivated independently of one another and alongside one another.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a computed tomography device, said method comprising:
   via a control computer of a computed tomography device, defining an extreme value of at least one scan parameter of the computed tomography device that affects at least one technical component selected from the group consisting of at least one x-ray tube, at least one slip ring for the transmission of data and/or energy, and at least one bearing for the rotating support of a rotatable part relative to a stationary part of a gantry of the computed tomography device; and
   via said control computer, setting an operating mode for the computed tomography device that reduces a load on said at least one technical component, wherein a settable value for the at least one scan parameter affecting the at least one technical component is limited to a predetermined percentage below or above the extreme value for the operation of the at least one technical component in said operating mode.

2. The method as claimed in claim 1, wherein the operating mode is a modified automatic dose system.

3. The method as claimed in claim 1, wherein the settable value for the tube current and/or the mean power consumption of the x-ray tube per rotation of the rotatable part of the gantry and/or the tube voltage and/or the size of the focus on the anode of the x-ray tube is limited as the scan parameter for the at least one x-ray tube.

4. The method as claimed in claim 3, wherein the size of the focus on the anode of the x-ray tube is set as a function of a scan protocol of the computed tomography device and/or of a certain examination of a patient.

5. The method as claimed in claim 1, wherein the settable value for the rotation speed and/or the pitch is limited as the scan parameter for the at least one slip ring or the at least one bearing.

6. The method as claimed in claim 1, wherein a tube load computer checks the feasibility of a certain examination of a patient for the scan parameters affecting the at least one x-ray tube.

7. The method as claimed in claim 1, wherein in the operating mode at least one operating function or at least one type of operation of the computed tomography device is deactivated.

8. The method as claimed in claim 7, wherein the sequence scan operating function or type of operation is deactivated.

9. The method as claimed in claim 1, providing said control device with a user interfacing having an actuatable button with which the operating mode is selectively activated and deactivated by a user.

10. The method as claimed in claim 1, comprising providing said control computer with a scan protocol for examination of a patient and determining, in said control computer, whether said scan protocol can be executed with the scan parameter affecting the at least one technical component being limited to the settable value, and, if not, setting the value for the scan parameter affecting the at least one technical component to the percentage below or above the extreme value and adjusting a value of another scan parameter of the scan protocol to permit the examination of the patient to take place with the scan protocol.

11. The method as claimed in claim 10, wherein the other scan parameter is the scan time.

12. The method as claimed in claim 1, comprising, at a graphical user interface of said control computer, displaying consequences associated with the operating mode for a scan of a patient and/or for image information relating to the patient that can be obtained further to a scan of a patient.

13. The method as claimed in claim 12, comprising displaying a designation of a lengthening of the scan time or a loss of achievable image quality.

14. The method as claimed in claim 13, comprising display the body region of the patient where and/or the degree to which a loss of image quality takes place.

15. The method as claimed in claim 1, wherein all the time during operation of the computed tomography device the use of the operating mode is logged and/or visualized.

16. The method as claimed in claim 15, comprising using logging of the use of the operating mode as a basis for calculating discounts granted to a customer of the computed tomography device in the context of a service agreement relating to the computed tomography device or to incentivize usage by a customer of the computed tomography device.

17. A non-transitory, computer-readable data storage medium encoded with programming instructions that, when said data storage medium is loaded into a computerized control device cause the control device to operate the computed tomography device to reduce a load on at least one technical component of the computed tomography device selected from the group consisting of at least one x-ray tube, at least one slip ring for the transmission of data and/or energy, and at least one bearing for the rotating support of a rotatable part relative to a stationary part of a gantry of the computed tomography device during operation of the at least one technical component by:
   for at least one scan parameter of the computed tomography device affecting said at least one technical component, defining an extreme value; and
   operating said computed tomography device in an operating mode wherein the settable value for said at least one scan parameter affecting said at least one technical component is limited to a predetermined percentage below or above said extreme value for the operation of said at least one technical component.

18. A computed tomography device comprising:
   at least one technical component that participates in operation of the computed tomography device selected from the group consisting of at least one x-ray tube, at least one slip ring for the transmission of data and/or energy, and at least one bearing for the rotating support of a rotatable part relative to a stationary part of a gantry of the computed tomography device;

a computerized control unit that operates said at least one technical component, said computerized control device being configured to operate said at least one technical component with at least one scan parameter that affects said at least one technical component and to define an extreme value for said at least one scan parameter; and said control device being configured to operate said at least one technical component in an operating mode wherein the settable value for said at least one scan parameter that affects said at least one technical component is limited to a predetermined percentage below or above said extreme value for said operation of said at least one technical component.

* * * * *